United States Patent [19]
Nakayama et al.

[11] Patent Number: 5,382,688
[45] Date of Patent: Jan. 17, 1995

[54] DIAMINO COMPOUNDS AND THEIR PRODUCTION METHOD

[75] Inventors: Minoru Nakayama, Kumamoto; Toshiya Sawai, Chiba; Masaharu Hayakawa, Chiba; Shizuo Murata, Chiba; Yukino Abe, Chiba, all of Japan

[73] Assignee: Chisso Corporation, Tokyo, Japan

[21] Appl. No.: 162,318

[22] Filed: Dec. 7, 1993

[30] Foreign Application Priority Data

Dec. 7, 1992 [JP] Japan .................. 4-351340
Dec. 7, 1992 [JP] Japan .................. 4-351341

[51] Int. Cl.⁶ .................................. C07C 211/54
[52] U.S. Cl. .................................... 564/322
[58] Field of Search ............................ 564/322

[56] References Cited

U.S. PATENT DOCUMENTS

| | | | |
|---|---|---|---|
| 2,883,365 | 4/1959 | Mathes | 260/45.95 |
| 3,247,199 | 4/1966 | Marxer et al. | 564/322 X |
| 5,008,456 | 4/1991 | Murata et al. | 564/322 |

OTHER PUBLICATIONS

Nigorikawa et al, Chemical Abstracts, vol. 110 (1989) 222725u.

Sutyagina et al, Chemical Abstracts, vol. 54 (1959) 12828g.

Primary Examiner—Richard L. Raymond
Attorney, Agent, or Firm—Wenderoth, Lind & Ponack

[57] ABSTRACT

The present invention is to provide diamino compounds useful to polyamide raw materials for production of liquid crystal alignment layers having excellent voltage holding ratios without development of image-sticking phenomena, a method for producing the compounds and liquid crystal display devices equipping the liquid crystal alignment layers.

The Diamino compounds are represented by the general formula (1):

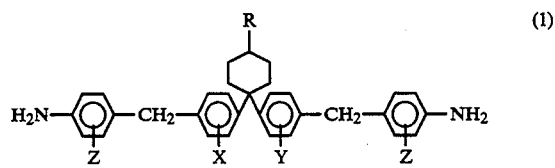

wherein R indicates hydrogen or an alkyl group having 1 to 8 carbon atoms, further, X, Y and Z indicate hydrogen, an alkyl group having 1 to 3 carbon atoms or fluorine, respectively, and a part or all of them may be the same or different, and the positions of these substitutive groups may be ortho positions or meta positions.

2 Claims, 6 Drawing Sheets

DIAMINO COMPOUNDS AND THEIR PRODUCTION METHOD

BACKGROUND OF THE INVENTION

The present invention relates to diamino compounds and liquid crystal alignment layers obtained from the compounds, more particularly, new diamino compounds, a method for producing the compounds, liquid crystal alignment layers having high pretilt angles, which is obtained by using the diamino compounds, and liquid crystal display devices equipping the liquid crystal alignment layers.

The main current of liquid crystal display devices which are used in conventional clocks, watches and electronic calculators is a twist nematic (abbreviated as TN hereinafter) mode having a structure in which molecular alignment of nematic liquid crystals is twisted at an angle of 90 degrees on the surface of a couple of upper and lower electrode substrates. Further, a supertwist nematic (abbreviated as STN hereinafter) mode in which the molecular alignment of nematic liquid crystals is twisted at angles of 180–300 degrees has been developed and then large panel liquid crystal display devices having excellent display quality are developing.

Moreover, in recent years, since matrix display or color display has been done, a MIM (metal-insulation layer-metal) device and a TFT (field effect type thin layer transistor) device are developing, and the MIM device adopts many pixel electrodes and an active type twist nematic mode which can switch ON-OFF against these electrodes.

As to problems shared by these modes, when the same scene is lighted up for a long time, an image-sticking phenomenon may be found after the scene has disappeared. Particularly, it is very important problems to improve the image-sticking phenomenon to obtain a liquid crystal display devices having high quality.

It is considered that the image-sticking phenomenon is due to electric double layers which are produced on the alignment layers surface by ion components of impurities contained in the liquid crystal since DC components are applied on the liquid crystal display device electric charge differences which are produced between upper and lower substrates, and electric potential differences from the stable electric charge differences. Particularly, in case of TFT devices, since DC components cannot be removed for characteristics of the devices, the image-sticking phenomenon is more conspicuous and serious than that of TN and STN.

Further, in TFT modes, high voltage holding ratios are required to prevent flicker of screens.

As an alignment layer used for such a liquid crystal display device, organic films such as polyimide and polyamide are mainly employed, and Japanese Publication of Unexamined Patent Application No. 51-65960 discloses a liquid crystal display device that is equipped with a liquid crystal alignment layer produced from a polyimide resin having a repeating unit represented by a formula:

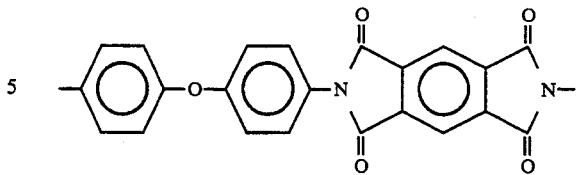

However, the polyimide alignment layer produced from such a polyether compound has a problem that the image-sticking phenomenon is apt to produce.

SUMMARY OF THE INVENTION

An object of the present invention is to solve the above problems and to provide liquid crystal alignment layers having an excellent voltage holding ratio without an image-sticking phenomenon and liquid crystal display devices obtained by using the films, diamino compounds useful to obtain the liquid crystal alignment layers and a method for producing the compounds.

The inventors of the present invention have studied earnestly and found that the image-sticking phenomenon mutually relates to polarity of the surface of alignment layers, and liquid crystal alignment layers and liquid crystal devices having an excellent voltage holding ratio without the image-sticking phenomenon is obtained by using diamino compounds having a certain structure by which the polarity can be small.

The diamino compound does not have polar atoms such as —O'and —SO$_2$—, and the ratio of imide groups is relatively reduced by increasing the amine molecular weight, and the ratio of polar components is extremely small.

The content of the present invention is explained in detail.

1) A diamino compound represented by a general formula (1):

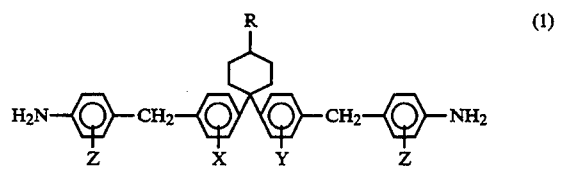

wherein R indicates hydrogen or an alkyl group having 1 to 8 carbon atoms, further, X, Y and Z indicate hydrogen, an alkyl group having 1 to 3 carbon atoms or fluorine, respectively, and a part or all of them may be the same or different, and the positions of these substitutive groups may be ortho positions or meta positions.

2) A method for producing a diamino compound represented by the general formula (1) in 1), which comprises condensing a para nitrobenzoyl chloride derivative represented by the formula (3):

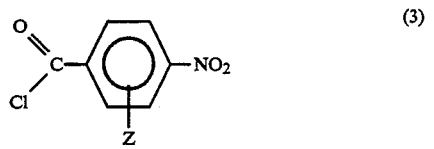

wherein Z indicates hydrogen, an alkyl group having 1 to 3 carbon atoms or fluorine, and the position of substitutive group Z may be an ortho position or a meta position, to a diphenylcyclohexane derivative represented by the formula (2):

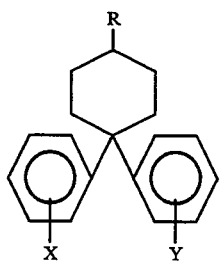
(2)

wherein R indicates hydrogen or an alkyl group having 1 to 8 carbon atoms, further, X and Y indicate hydrogen, an alkyl group having 1 to 3 carbon atoms or fluorine, respectively, and a part or all of them may be the same or different, and the positions of these substitutive groups may be ortho positions or meta positions, and reducing a carbonyl group and a nitro group to obtain the diamino compound.

3) A liquid crystal alignment layer containing as a principal constituent a polymer having a diamino compound represented by the general formula (1) in 1) in a long chain of the molecule.

4) A liquid crystal alignment layer containing as a principal constituent a polyimide having a structure unit represented by the general formula (4):

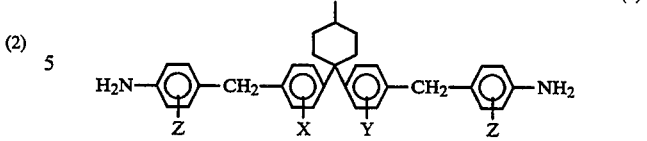
(1)

wherein R indicates hydrogen or an alkyl group having 1 to 8 carbon atoms, further, X, Y and Z indicate hydrogen, an alkyl group having 1 to 3 carbon atoms or fluorine, respectively, and a part or all of them may be the same or different, and the positions of these substitutive groups may be ortho positions or meta positions, and A is an aromatic group of four valences, an aliphatic group of four valences or a complex group having aromatic and aliphatic properties of four valences.

6) A liquid crystal display device equipping the liquid crystal alignment layer as described in 3).

7) A liquid crystal display device equipping the liquid crystal alignment layer as described in 4).

8) A liquid crystal display device as in 6), it uses a nematic liquid crystal mixture having positive dielectric anisotropy.

9) A liquid crystal display device as in 7), it uses a nematic liquid crystal mixture having positive dielectric anisotropy.

The diamino compounds of the present invention are represented by the above formula (1) and exemplified

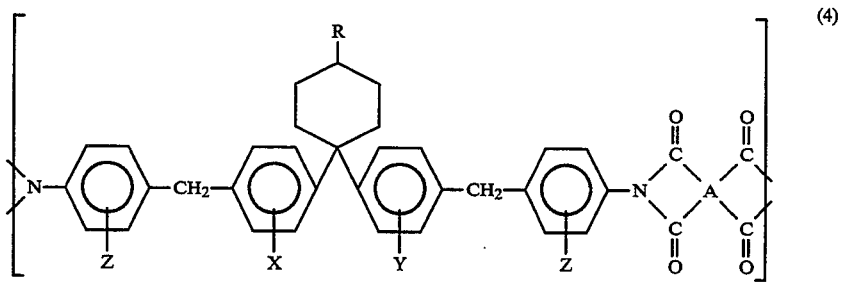
(4)

wherein R indicates hydrogen or an alkyl group having 1 to 8 carbon atoms, further, X, Y and Z indicate hydrogen, an alkyl group having 1 to 3 carbon atoms or fluorine, respectively, and a part or all of them may be the same or different, and the positions of these substitutive groups may be ortho positions or meta positions, and A is an aromatic group of four valences, an aliphatic group of four valences or a complex group having aromatic and aliphatic properties of four valences.

5) A liquid crystal alignment layer as in 5), the polyimide is obtained by reacting a tetracarboxylic dianhydride represented by the following formula (5) and a diamino compound represented by the following formula (1) in a solvent to produce a polyamic acid and heating the resultant polyamic acid.

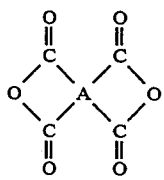
(5)

by the following compounds.
1,1-bis[4-(4-aminobenzyl)phenyl]cyclohexane,
1,1-bis[4-(4-aminobenzyl)phenyl]-4-methylcyclohexane,
1,1-bis[4-(4-aminobenzyl)phenyl]-4-ethylcyclohexane,
1,1-bis[4-(4-aminobenzyl)phenyl]-4-propylcyclohexane,
1,1-bis[4-(4-aminobenzyl)phenyl]-4-butylcyclohexane,
1,1-bis[4-aminobenzyl)phenyl]-4-pentylcyclohexane,
1,1-bis[4-aminobenzyl)phenyl]-4-hexylcyclohexane,
1,1-bis[4-aminobenzyl)phenyl]-4-heptylcyclohexane,
1,1-bis[4-aminobenzyl)phenyl]-4-octylcyclohexane,
1,1-bis[4-(4-amino-3-methylbenzyl)phenyl]-4-methylcyclohexane,
1,1-bis[4-(4-amino-3-methylbenzyl)phenyl]-4-ethylcyclohexane,
1,1-bis[4-(4-amino-3-methylbenzyl)phenyl]-4-propylcyclohexane,
1,1-bis[4-(4-amino-3-methylbenzyl)phenyl]-4-butylcyclohexane,
1,1-bis[4-(4-amino-3-methylbenzyl)phenyl]-4-pentylcyclohexane,
1,1-bis[4-(4-amino-3-methylbenzyl)phenyl]-4-hexylcyclohexane,
1,1-bis[4-(4-amino-3-methylbenzyl)phenyl]-4-heptylcyclohexane, 1,1-bis[4-(4-amino-3-methylbenzyl)phenyl]-4-octylcyclohexane,
1,1-bis[4-(4-aminobenzyl)-3-methylphenyl]-4-methylcyclohexane,
1,1-bis[4-(4-aminobenzyl)-3-methylphenyl]-4-ethylcyclohexane,
1,1-bis[4-(4-aminobenzyl)-3-methylphenyl]-4-propylcyclohexane,
1,1-bis[4-(4-aminobenzyl)-3-methylphenyl]-4-butylcyclohexane,
1,1-bis[4-(4-aminobenzyl)-3-methylphenyl]-4-pentylcyclohexane,
1,1-bis[4-(4-aminobenzyl)-3-methylphenyl]-4-hexylcyclohexane,
1,1-bis[4-(4-aminobenzyl)-3-methylphenyl]-4-heptylcyclohexane,
1,1-bis[4-(4-aminobenzyl)-3-methylphenyl]-4-octylcyclohexane,
1,1-bis[4-(4-aminobenzyl)-2-methylphenyl]-4-methylcyclohexane,
1,1-bis[4-(4-aminobenzyl)-2-methylphenyl]-4-ethylcyclohexane,
1,1-bis[4-(4-aminobenzyl)-2-methylphenyl]-4-propylcyclohexane,
1,1-bis[4-(4-aminobenzyl)-2-methylphenyl]-4-butylcyclohexane,
1,1-bis[4-(4-aminobenzyl)-2-methylphenyl]-4-pentylcyclohexane,
1,1-bis[4-(4-aminobenzyl)-2-methylphenyl]-4-hexylcyclohexane
1,1-bis[4-(4-aminobenzyl)-2-methylphenyl]-4-heptylcyclohexane,
1,1-bis[4-(4-aminobenzyl)-2-methylphenyl]-4-octylcyclohexane,
1,1-bis[4-(4-amino-3-methylbenzyl)phenyl]cyclohexane,
1,1-bis[4-(4-amino-3-ethylbenzyl)phenyl]cyclohexane,
1,1-bis[4-(4-amino-3-propylbenzyl)phenyl]cyclohexane,
1,1-bis[4-(4-amino-3-fluorobenzyl)phenyl]cyclohexane,
1,1-bis[4-(4-aminobenzyl)-3-methylphenyl]cyclohexane,
1,1-bis[4-(4-aminobenzyl)-3-ethylphenyl]cyclohexane,
1,1-bis[4-(4-aminobenzyl)-3-propylphenyl]cyclohexane,
1,1-bis[4-(4-aminobenzyl)-3-fluorophenyl]cyclohexane,
1,1-bis[4-(4-amino-3-ethylbenzyl)phenyl]-4-methylcyclohexane,
1,1-bis[4-(4-amino-3-propylbenzyl)phenyl]-4-methylcyclohexane,
1,1-bis[4-(4-amino-3-fluorobenzyl)phenyl]-4-methylcyclohexane,
1,1-bis[4-(4-aminobenzyl)-3-ethylphenyl]-4-methylcyclohexane,
1,1-bis[4-(4-aminobenzyl)-3-propylphenyl]-4-methylcyclohexane,
1,1-bis[4-(4-aminobenzyl)-3-fluorophenyl]-4-methylcyclohexane,
1,1-bis[4-amino-3-ethylbenzyl)phenyl]-4-ethylcyclohexane,
1,1-bis[4-amino-3-propylbenzyl)phenyl]-4-ethylcyclohexane,
1,1-bis[4-amino-3-fluorobenzyl)phenyl]-4-ethylcyclohexane,
1,1-bis[4-(4-aminobenzyl)-3-ethylphenyl]-4-ethylcyclohexane,
1,1-bis[4-(4-aminobenzyl)-3-propylphenyl]-4-ethylcyclohexane,
1,1-bis[4-(4-aminobenzyl)-3-fluorophenyl]-4-ethylcyclohexane,
1,1-bis[4-(4-amino-3-ethylbenzyl)phenyl]-4-propylcyclohexane,
1,1-bis[4-(4-amino-3-propylbenzyl)phenyl]-4-propylcyclohexane,
1,1-bis[4-(4-amino-3-fluorobenzyl)phenyl]-4-propylcyclohexane,
1,1-bis[4-(4-aminobenzyl)-3-ethylphenyl]-4-propylcyclohexane,
1,1-bis[4-(4-aminobenzyl)-3-propylphenyl]-4-propylcyclohexane, and
1,1-bis[4-(4-aminobenzyl)-3-fluorophenyl]-4-propylcyclohexane.

The production of the diamino compounds of the present invention is described by embodiment.

Diphenylcyclohexanes and their derivatives which are used in the present invention are represented by above-mentioned formula (2) and exemplified by the following compounds.
1,1-diphenylcyclohexane,
1,1-diphenyl-4-methylcyclohexane,
1,1-diphenyl-4-ethylcyclohexane,
1,1-diphenyl-4-propylcyclohexane,
1,1-diphenyl-4-butylcyclohexane,
1,1-diphenyl-4-pentylcyclohexane,
1,1-diphenyl-4-hexylcyclohexane,
1,1-diphenyl-4-heptylcyclohexane,
1,1-diphenyl-4-octylcyclohexane,
1,1-bis(2-methylphenyl)cyclohexane,
1,1-bis(2-methylphenyl)-4-methylcyclohexane,
1,1-bis(2-methylphenyl)-4-ethylcyclohexane,
1,1-bis(2-methylphenyl)-4-propylcyclohexane,
1,1-bis(2-methylphenyl)-4-butylcyclohexane,
1,1-bis(2-methylphenyl)-4-pentylcyclohexane,
1,1-bis(2-methylphenyl)-4-hexylcyclohexane,
1,1-bis(2-methylphenyl)-4-heptylcyclohexane,
1,1-bis(2-methylphenyl)-4-octylcyclohexane.
1,1-bis(3-methylphenyl)cyclohexane,
1,1-bis(3-methylphenyl)-4-methylcyclohexane,
1,1-bis(3-methylphenyl)-4-ethylcyclohexane,
1,1-bis(3-methylphenyl)-4-propylcyclohexane,
1,1-bis(3-methylphenyl)-4-butylcyclohexane,
1,1-bis(3-methylphenyl)-4-pentylcyclohexane,
1,1-bis(3-methylphenyl)-4-hexylcyclohexane,
1,1-bis(3-methylphenyl)-4-heptylcyclohexane,
1,1-bis(3-methylphenyl)-4-octylcyclohexane.
1,1-bis(2-ethylphenyl)cyclohexane,
1,1-bis(2-ethylphenyl)-4-methylcyclohexane,
1,1-bis(2-ethylphenyl)-4-ethylcyclohexane,
1,1-bis(2-ethylphenyl)-4-propylcyclohexane,
1,1-bis(2-ethylphenyl)-4-butylcyclohexane,
1,1-bis(2-ethylphenyl)-4-pentylcyclohexane,
1,1-bis(2-ethylphenyl)-4-hexylcyclohexane,
1,1-bis(2-ethylphenyl)-4-heptylcyclohexane,
1,1-bis(2-ethylphenyl)-4-octylcyclohexane.
1,1-bis(3-ethylphenyl)cyclohexane,
1,1-bis(3-ethylphenyl)-4-methylcyclohexane,
1,1-bis(3-ethylphenyl)-4-ethylcyclohexane,
1,1-bis(3-ethylphenyl)-4-propylcyclohexane,
1,1-bis(3-ethylphenyl)-4-butylcyclohexane,
1,1-bis(3-ethylphenyl)-4-pentylcyclohexane,
1,1-bis(3-ethylphenyl)-4-hexylcyclohexane,
1,1-bis(3-ethylphenyl)-4-heptylcyclohexane,
1,1-bis(3-ethylphenyl)-4-octylcyclohexane.
1,1-bis(2-propylphenyl)cyclohexane,
1,1-bis(2-propylphenyl)-4-methylcyclohexane,
1,1-bis(2-propylphenyl)-4-ethylcyclohexane,
1,1-bis(2-propylphenyl)-4-propylcyclohexane,
1,1-bis(2-propylphenyl)-4-butylcyclohexane, 1,1-bis(2-propylphenyl)-4-pentylcyclohexane,
1,1-bis(2-propylphenyl)-4-hexylcyclohexane,
1,1-bis(2-propylphenyl)-4-heptylcyclohexane,
1,1-bis(2-propylphenyl)-4-octylcyclohexane.
1,1-bis(3-propylphenyl)cyclohexane,
1,1-bis(3-propylphenyl)-4-methylcyclohexane,
1,1-bis(3-propylphenyl)-4-ethylcyclohexane,
1,1-bis(3-propylphenyl)-4-propylcyclohexane,
1,1-bis(3-propylphenyl)-4-butylcyclohexane,
1,1-bis(3-propylphenyl)-4-pentylcyclohexane,
1,1-bis(3-propylphenyl)-4-hexylcyclohexane,
1,1-bis(3-propylphenyl)-4-heptylcyclohexane,
1,1-bis(3-propylphenyl)-4-octylcyclohexane.
1,1-bis(2-fluorophenyl)cyclohexane,
1,1-bis(2-fluorophenyl)-4-methylcyclohexane,
1,1-bis(2-fluorophenyl)-4-ethylcyclohexane,
1,1-bis(2-fluorophenyl)-4-propylcyclohexane,
1,1-bis(2-fluorophenyl)-4-butylcyclohexane,
1,1-bis(2-fluorophenyl)-4-pentylcyclohexane,
1,1-bis(2-fluorophenyl)-4-hexylcyclohexane,
1,1-bis(2-fluorophenyl)-4-heptylcyclohexane,
1,1-bis(2-fluorophenyl)-4-octylcyclohexane.
1,1-bis(3-fluorophenyl)cyclohexane,
1,1-bis(3-fluorophenyl)-4-methylcyclohexane,
1,1-bis(3-fluorophenyl)-4-ethylcyclohexane,
1,1-bis(3-fluorophenyl)-4-propylcyclohexane,
1,1-bis(3-fluorophenyl)-4-butylcyclohexane,
1,1-bis(3-fluorophenyl)-4-pentylcyclohexane,
1,1-bis(3-fluorophenyl)-4-hexylcyclohexane,
1,1-bis(3-fluorophenyl)-4-heptylcyclohexane, and
1,1-bis(3-fluorophenyl)-4-octylcyclohexane.

If necessary, two or more kinds of these compounds may be used at the same time. These diphenylcyclohexanes or derivatives can be obtained in reduction of a carbonyl group of a diphenylcyclohexanone derivative; in a process comprising producing an alcohol by a Grignard reaction of the diphenylcyclohexanone derivative and alkylmagnesium halide, dehydrating the alcohol, and reducing the double bond of the resulting compound by a method such as catalytic hydrogen reduction; or in a process comprising reacting a diphenylcyclohexanone derivative with an alkyl lithium, dehydrating the resulting alcohol and reducing the double bond of the resulting compound by a method such as catalytic hydrogen reduction.

Paranitrobenzoyl chlorides or their derivatives which are used in the present invention are represented by the above formula (3) and exemplified by the following compounds.
4-nitrobenzoylchloride,
2-methyl-4-nitrobenzoylchloride,
2-ethyl-4-nitrobenzoylchloride,
2-propyl-4-nitrobenzoylchloride,
2-fluoro-4-nitrobenzoylchloride,
3-methyl-4-nitrobenzoylchloride,
3-ethyl-4-nitrobenzoylchloride,
3-propyl-4-nitrobenzoylchloride, and
3-fluoro-4-nitrobenzoylchloride.

If necessary, two or more kinds of these compounds may be used at the same time.

In the reaction of diphenylcyclohexanes or their derivatives with paranitrobenzoylchlorides or their derivatives, usually, catalysts are used. As such catalysts, $AlCl_3$, $SbCl_5$, $FeCl_3$, $TeCl_2$, $SnCl_4$, $TiCl_4$, $BiCl_3$, $ZnCl_2$ and the like are exemplified, $AlCl_3$ is preferred in the reactivity.

Further, if necessary solvents are used in the reaction. Such solvents are carbon disulfide, dichloromethane, chloroform, dichloroethane, nitrobenzene and the like, preferably nitrobenzene.

The reaction should be attained by mixing with stirring a catalyst and paranitrobenzoyl chloride or the derivative in a solvent or in absence of the solvent, adding dropwise diphenylcyclohexane or the derivative (if necessary dissolved in a solvent) at 0° C. to 150° C., and reacting these compounds. When the reaction velocity decreases, the reaction temperature can be raised and not to over 150° C.

After the reaction is stopped, the reaction mixture was poured over ice to inactivate the catalyst, the mixture was washed with water and the solvent was distilled away by, for example, steam distillation to obtain a purified 1,1-bis[4-(4-aminobenzyl)phenyl]cyclohexane derivative.

The reduction of carbonyl groups may be conducted by reaction with a trialkyl silane, concretely triethyl silane in the presence of a catalyst such as trifluoromethane sulfonic acid or titanium tetrachloride. The reaction temperature is preferably 0° C. to 100° C. In the reaction, a solvent may be used, and a halogenated hydrocarbon such as dichloromethane, chloroform or dichloroethane is preferably used.

The reduction of nitro groups may be conducted by hydrogen reduction in a solvent such as toluene, xylene, methanol, ethanol and tetrahydrofuran in the presence of a catalyst such as platinum-carbon, platinum oxide, Raney nickel, paladium-carbon (abbreviated as Pd-C hereinafter) and the like at atmospheric pressure or under pressure at a temperature of 10°-80° C.

The aimed diamino compounds can be produced by optional selection of the substitute groups R, X, Y and Y of the above formulas (2) and (3).

Tetracarboxylic dianhydrides used in the liquid crystal alignment layers of the present invention may be aromatic or aliphatic types or complex types having aromatic and aliphatic properties. They are not limited but include for instance pyromellitic dianhydride, 3,3′,4,4′-biphenyltetracarboxylic dianhydride, 2,2′,3,3′-biphenyltetracarboxylic dianhydride, 2,3,3′,4′-biphenyltetracarboxylic dianhydride, 3,3′,4,4′-benzophenonetetracarboxylic dianhydride, 2,3,3′,4′-benzophenonetetracarboxylic dianhydride, 2,2′,3,3′-benzophenonetetracarboxylic dianhydride, bis(3,4-dicarboxyphenyl)ether dianhydride, bis(3,4-dicarboxyphenyl)sulfone dianhydride, 1,2,5,6-naphthalenetetracarboxylic dianhydride, 2, 3, 6, 7-naphthalenetetracarboxylic dianhydride, bis(dicarboxyphenyl)methane dianhydride, cyclobutanetetracarboxylic dianhydride, cyclopentanetetracarboxylic dianhydride, cyclohexanetetracarboxylic dianhydride, dicyclohexanetetracarboxylic dianhydride, dicyclopentanetetracarboxylic dianhydride, bis(dicarboxycyclohexyl)ether dianhydride, bis(dicarboxycyclohexyl)sulfone dianhydride, bis(dicarboxycyclohexyl)methane dianhydride, and

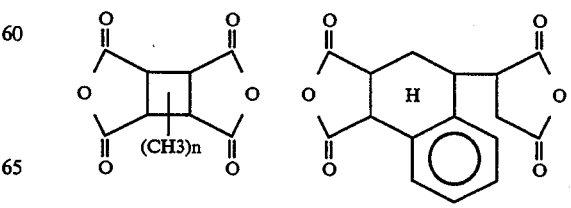

wherein n indicates a real number of 0–4.

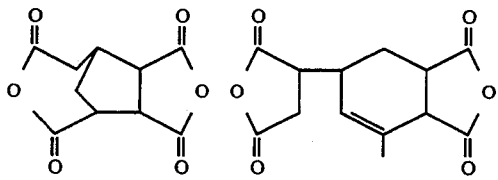

Some of these compounds may contain isomers, and these may be a mixture of the isomers. Further, it is unnecessary to limit the tetracarboxylic dianhydrides used in the present invention to the above cited compounds.

In the liquid crystal alignment layers of the present invention, it is possible to increase the adhesivity of the alignment layers on the substrates by using aminosilicon compounds or diaminosilicon compounds.

The aminosilicon compounds can be concretely exemplified as follows:

3-aminopropyltrimethoxysilane, 3-aminopropyltriethoxysilane, 3-aminopropylmethyldimethoxysilane, 3-aminopropylmethyldiethoxysilane, 3-aminopropyltris(2-methoxyethoxy) silane, 2-aminoethyltrimethoxysilane, 2-aminoethyltriethoxysilane, 2-aminoethylmethyldimethoxysilane, 2-aminoethylmethyldiethoxysilane, 4-aminobutyltrimethoxysilane, 4-aminophenyltrimethoxysilane, 4-aminophenyltriethoxysilane, 4-aminophenylmethyldimethoxysilane, 4-aminophenylmethyldiethoxysilane, 4-aminophenyltris(2-methoxyethoxy) silane, 3-(4-aminophenyl)propyltrimethoxysilane, 3-(4-aminophenyl)propyltriethoxysilane, 3-aminophenyltrimethoxysilane, 3-aminophenyltriethoxysilane, 3-(4-aminophenyl)propylmethyldimethoxysilane, 3-(4-aminophenyl)propylmethyldiethoxysilane, 3-aminophenylmethyldimethoxysilane, and 3-aminophenylmethyldiethoxysilane.

When the aminosilicon compounds are added to the polyimide-type polymers, the content is 50 mol % or less of the polyimide raw materials, preferably 30 mol % or less.

Further, the diaminosilicon compounds represented by the formula:

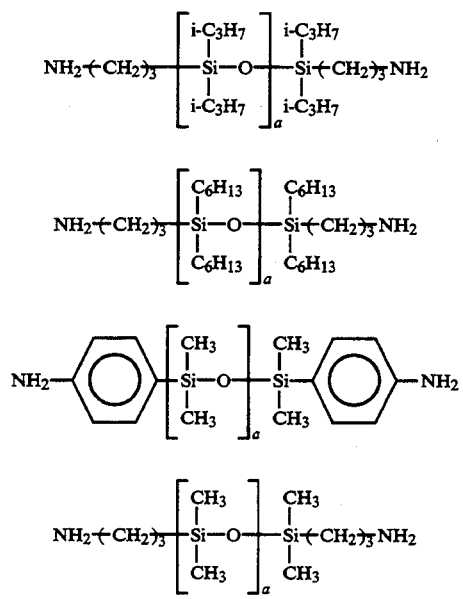

wherein a indicates an integer of 0-4. When these diaminosilicon compounds are added to the polyimide-type polymers, the diaminosilicon compounds can be replaced by 50 mol % or less, preferably 30 mol % or less of the diamino compounds which are polyimide raw materials.

For providing the liquid crystal alignment layer of the present invention on a substrate, preferably, a precursor polyamic acid which is obtained by condensation of a tetracarboxylic dianhydride and a diamino compound is applied on the substrate, and the substrate is heated to produce a polyimide-type polymer film on the substrate by dehydration. More concretely, polyamic acid is dissolved in a solvent such as N-methyl-2-pyrrolidone (NMP), dimethylacetamide (DMAc), dimethylformamide (DMF), dimethylsulfoxide (DMSO), butylcellosolve or ethylcarbitol, the solution is adjusted to 0.1–30% by weight, preferably 1–10% by weight, and the resulting solution is applied on the substrate by a method such as a brush method, a dipping method, a rotation coating method, a spray method, a printing method and the like to form an applied film. After the application, the solvent is vaporized at 50°–150° C., preferably 80°–120° C., and then the substrate is heated at 150°–400° C., preferably 180°–280° C. to form a polybenzylimide-type polymer film by dehydration and ring closure of the precursor. Before coating with the precursor, the surface of the substrate is treated with a silane coupling agent, and then the polymer film is formed, so that the adhesivity of the polymer film to the substrate can be improved. The obtained film surface is then repeatedly rubbed in the same direction, and a liquid crystal alignment layer is obtained.

On the substrate used as a liquid crystal display device, usually electrodes, concretely transparent electrodes of ITO (indium oxide-tin oxide) or tin oxide are formed. Further, an undercoat film such as an insulating film for preventing alkali elution from the substrate, a color filter, color filter overcoat and the like may be prepared between the electrodes and the substrate, and an overcoat film such as an insulating film, a color filter film and the like may be prepared on the electrodes. The constitution of these electrodes, the undercoat and the like in a liquid crystal cell can be the same as that of conventional liquid crystal display devices.

Using the substrate prepared by the above process, a liquid crystal display device is prepared by forming a cell, injecting a liquid crystal into the cell and sealing the cell. Otherwise, liquid crystals are spread on substrates, then the substrates are piled and sealed not to leak the liquid crystals, and a liquid crystal display device is produced. As the enclosure of the liquid crystal, conventional nematic liquid crystals, or several kinds of liquid crystals to which a bicolor pigment is added can be used.

A nematic liquid crystal mixture having positive dielectric anisotropy is preferably used as a liquid crystal display device of the present invention. As components for obtaining the liquid crystal compounds, there are (A) compounds having high dielectric anisotropy of $\Delta\epsilon \geq 5$, (B) compounds having low dielectric anisotropy of $\Delta\epsilon < 5$, (C) compounds having a transparency over 80° C., and (D) the other nematic liquid crystals. These liquid crystals are used as a mixture selected from the above (A) to (D) to control threshold voltages, viscosities, liquid crystal temperature ranges and the like to meet conditions for using display devices. In the above (B) to (D), some compounds have negative dielectric anisotropy. However, if the final nematic liquid crystal mixture having positive dielectric anisotropy is obtained by optional mixing, these compounds may be used in spite of the negative dielectric anisotropy.

As the compounds of (A), the following compounds are exemplified.

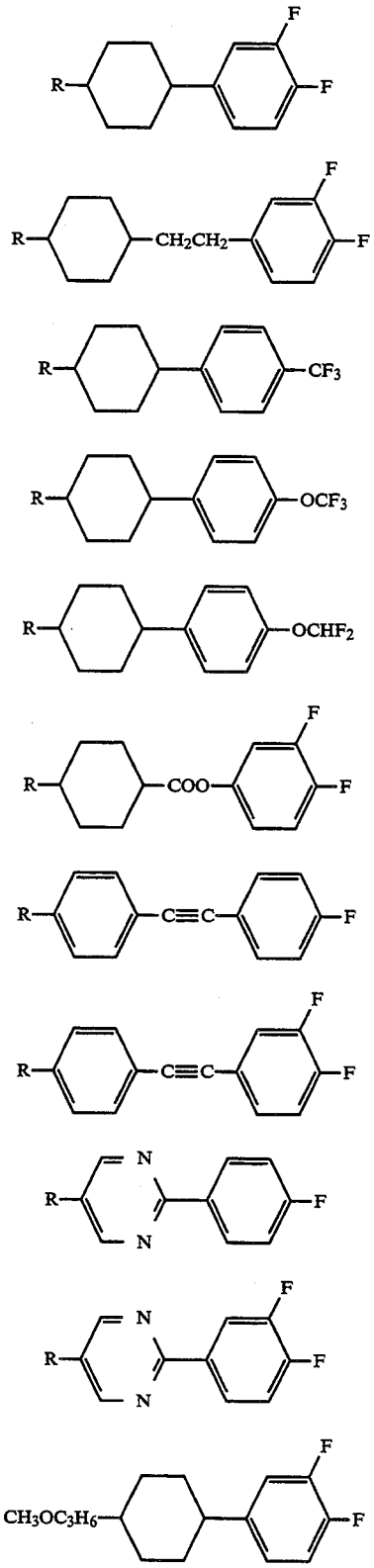

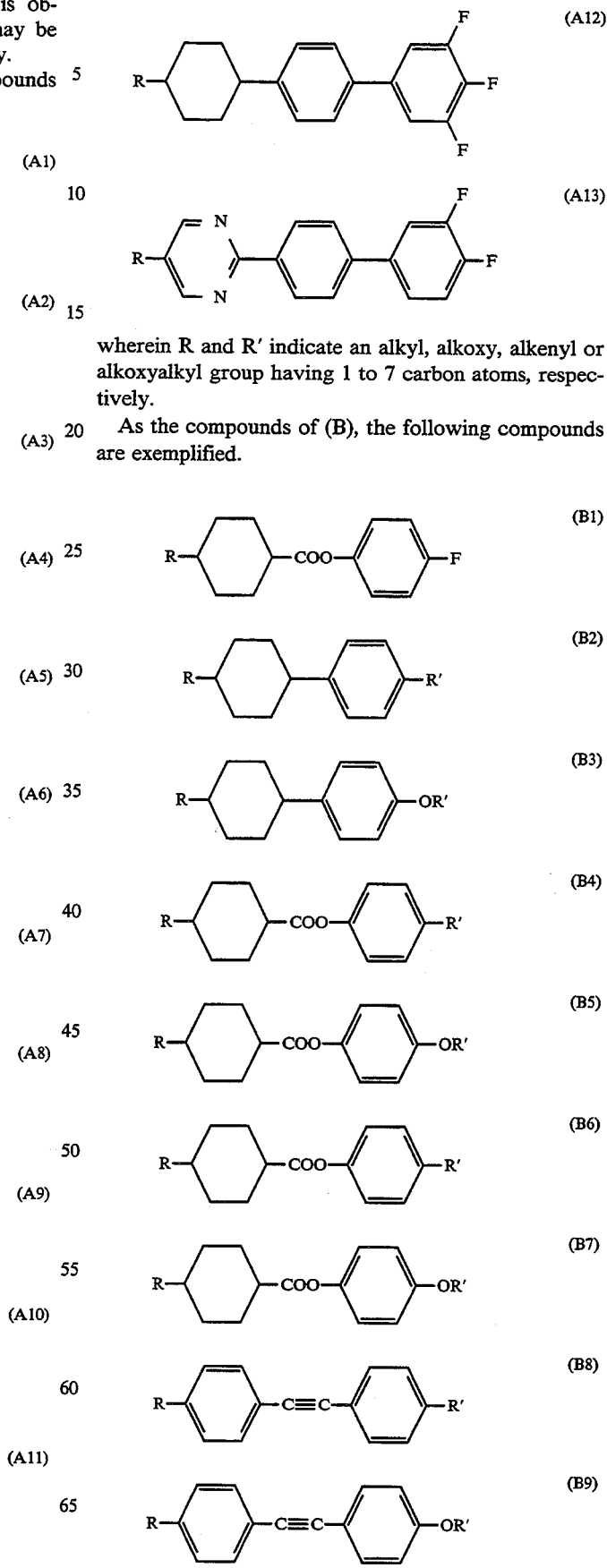

wherein R and R' indicate an alkyl, alkoxy, alkenyl or alkoxyalkyl group having 1 to 7 carbon atoms, respectively.

As the compounds of (B), the following compounds are exemplified.

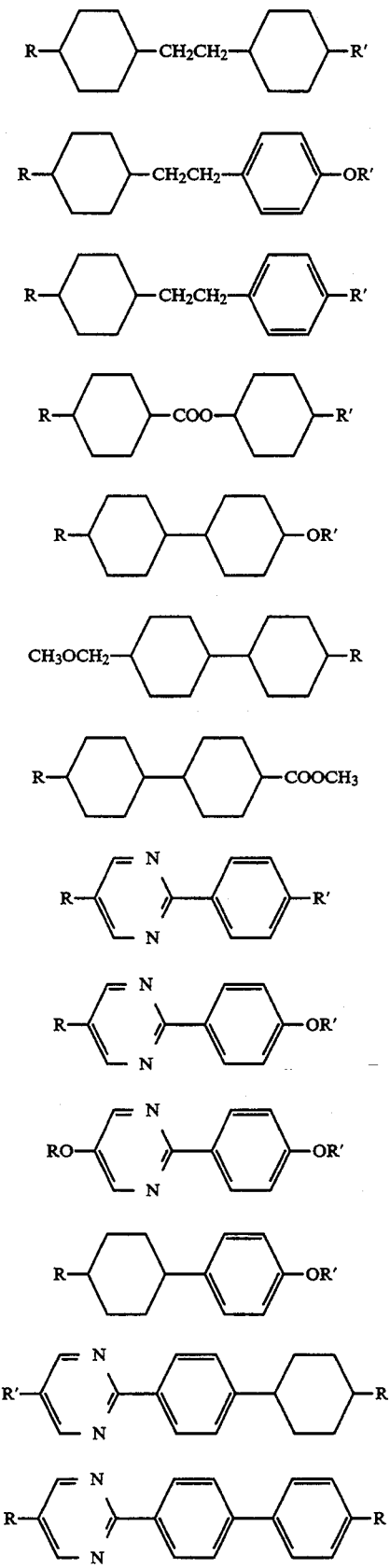
As the compounds of (C), the following compounds are exemplified.

-continued

[structural formula] (C37)

[structural formula] (C38)

[structural formula] (C39)

[structural formula] (C40)

[structural formula] (C41)

[structural formula] (C42)

[structural formula] (C43)

[structural formula] (C44)

[structural formula] (C45)

[structural formula] (C14)

[structural formula] (C15)

[structural formula] (C16)

[structural formula] (C17)

[structural formula] (C18)

[structural formula] (C19)

[structural formula] (C20)

[structural formula] (C21)

-continued

[structural formula] (C22)

[structural formula] C(23)

[structural formula] (C24)

[structural formula] (C25)

[structural formula] (C26)

[structural formula] (C27)

[structural formula] (C28)

[structural formula] (C29)

[structural formula] (C30)

[structural formula] (C46)

[structural formula] (C47)

[structural formula] (C48)

[structural formula] (C49)

[structural formula] (C50)

[structural formula] (C51)

[structural formula] (C52)

[structural formula] (C53)

[structural formula] (C54)

-continued
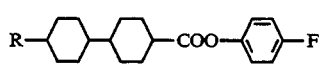 (C55)
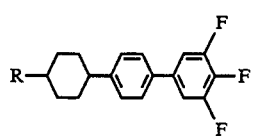 (C56)
As the compounds of (D), the following compounds are exemplified.
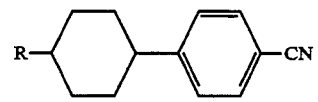 (D1)
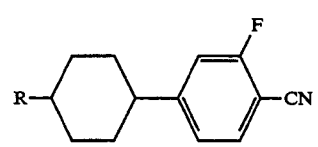 (D2)
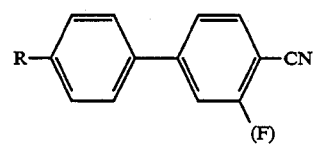 (D3)
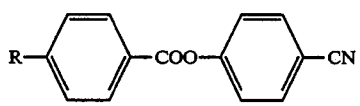 (D4)
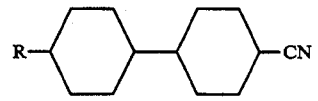 (D5)
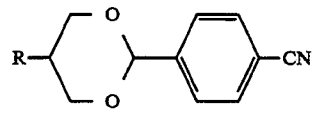 (D6)
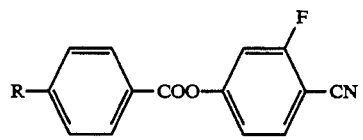 (D7)
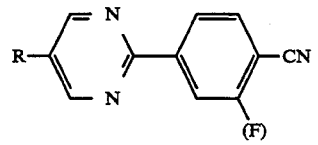 (D8)
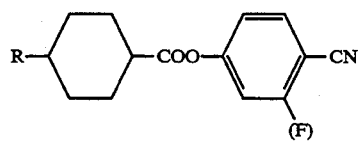 (D9)
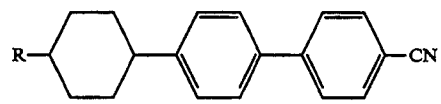 (D10)
-continued
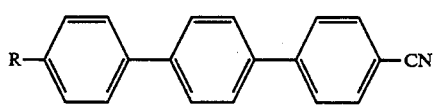 (D11)
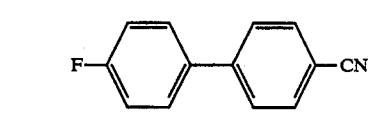 (D12)
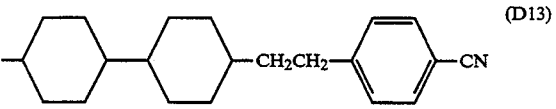 (D13)
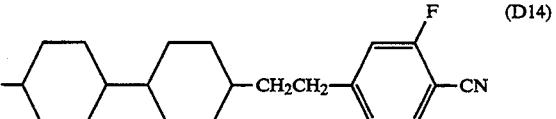 (D14)
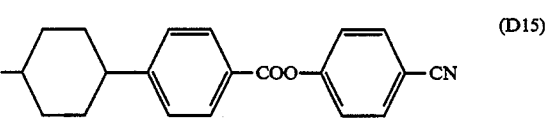 (D15)
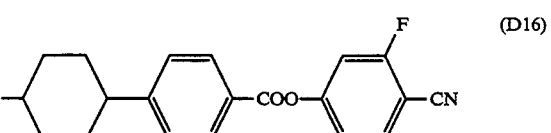 (D16)
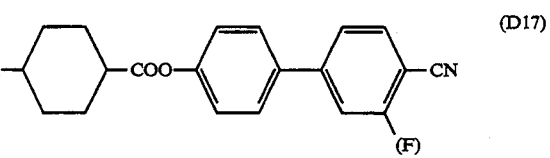 (D17)
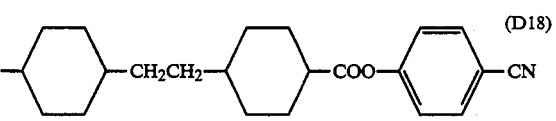 (D18)
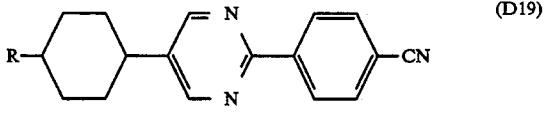 (D19)
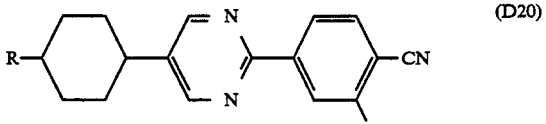 (D20)
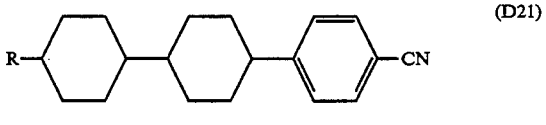 (D21)
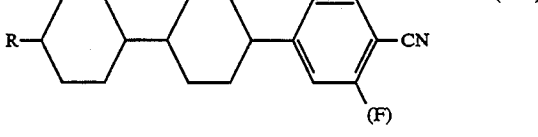 (D22)

In the above compounds (B)-(D), R and R' indicate an alkyl, alkoxy, alkenyl or alkoxyalkyl group having 1 to 7 carbon atoms, respectively.

As the nematic liquid crystal mixture used in the present invention, all compounds other than the above-mentioned compounds may be used without departing from the scope of the invention. The liquid crystal display devices of the present invention are characterized in that they have alignment control films which have little image-sticking phenomenon, the voltage holding ratio is high, the aligning properties of the liquid crystal is good and the pretilt angle is as high as that of polyetherimide-type polyimides

Figure 2:
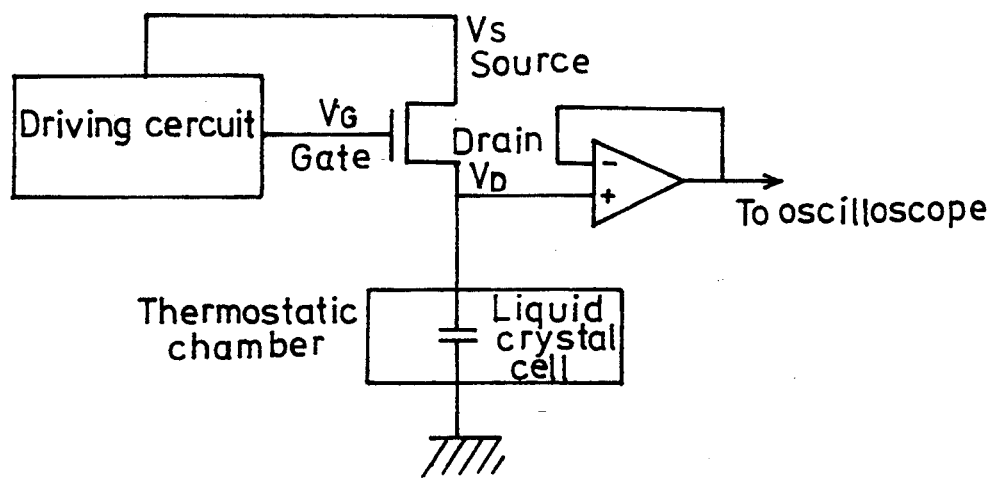
FIG. 2 is a circuit for measuring voltage holding ratios.

$V_D$ shows a wave form which is read out of an oscilloscope by applying $V_s$ to the circuit source of FIG. 2.

Figure 4:
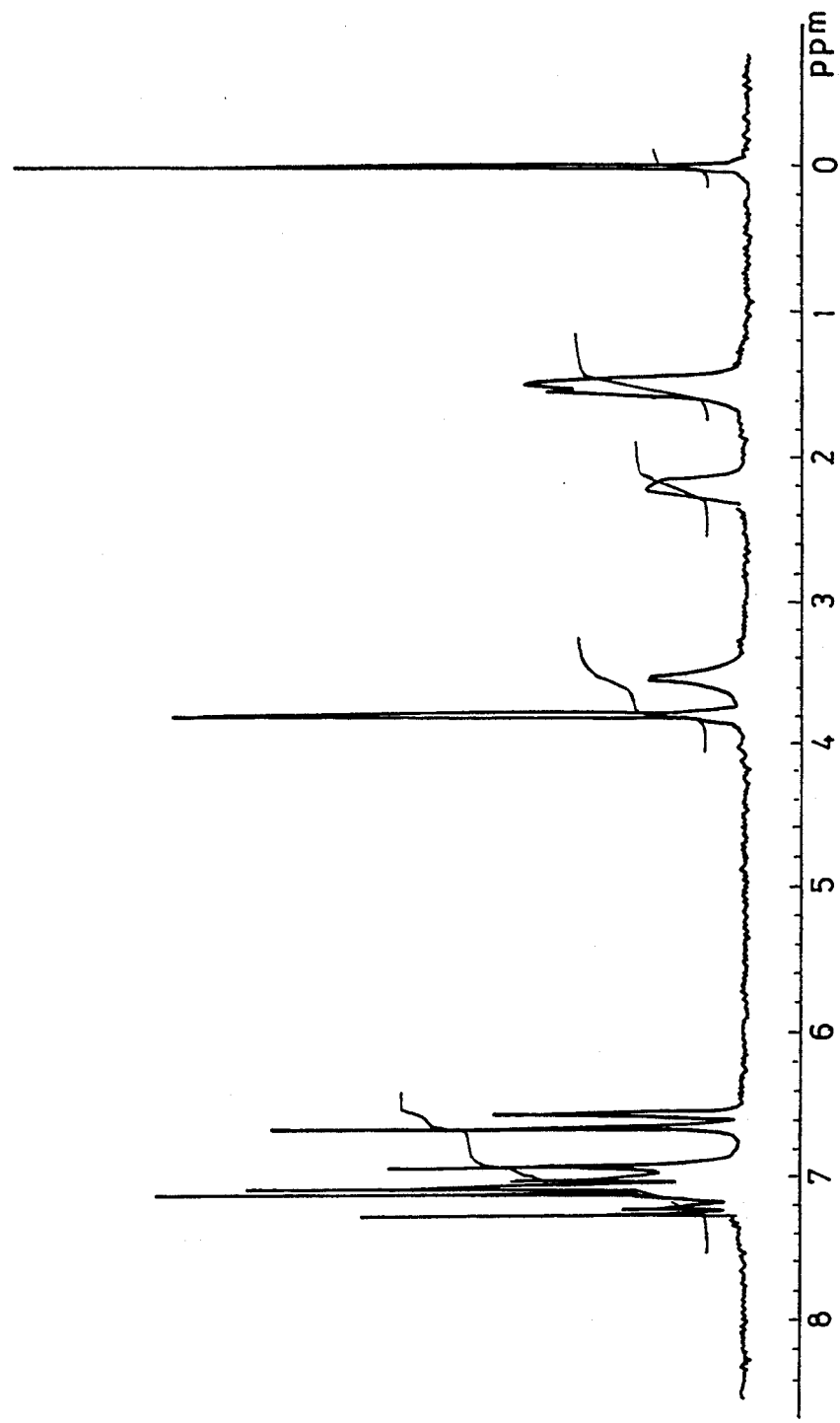

FIG. 4 is a $^1$H-NMR spectrum chart of the diamino compound obtained in Example 1.

Figure 5:
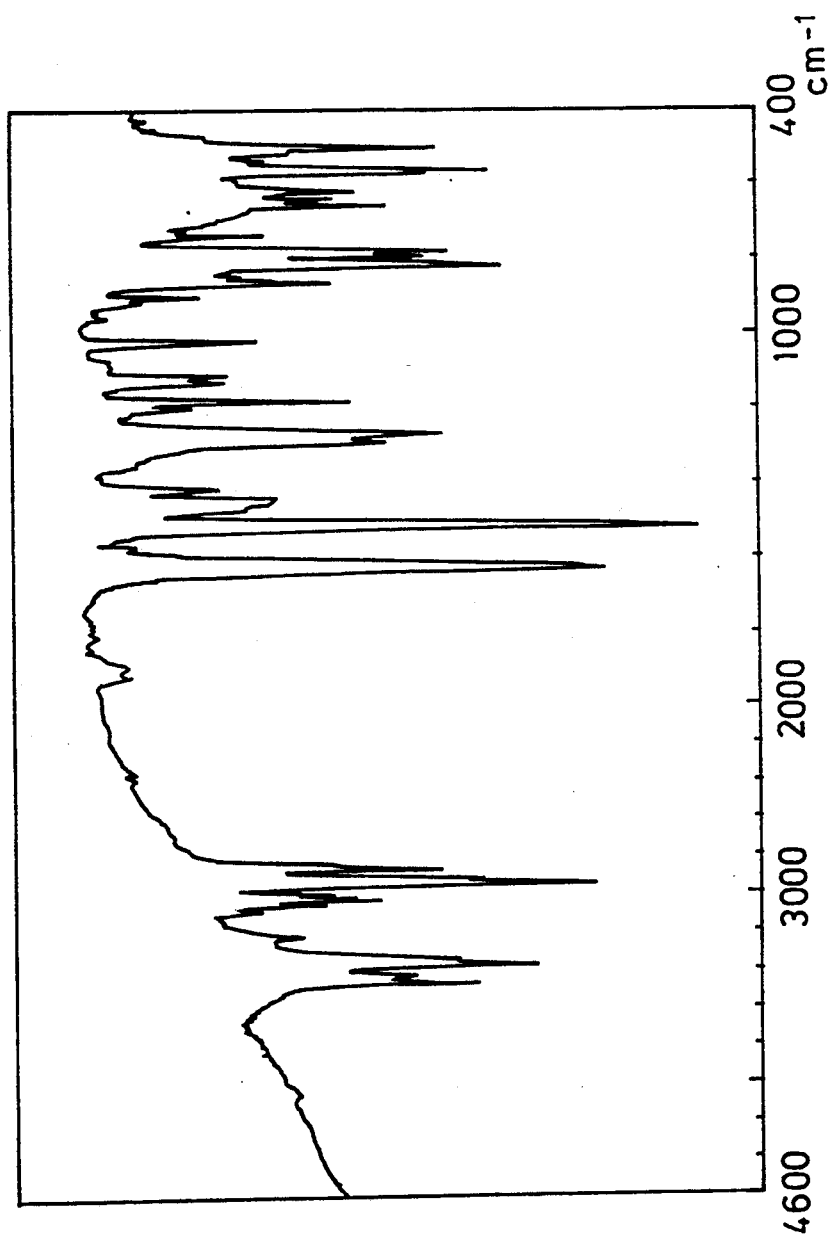

FIG. 5 is an IR chart of the diamino compound obtained in Example 1.

Figure 6:
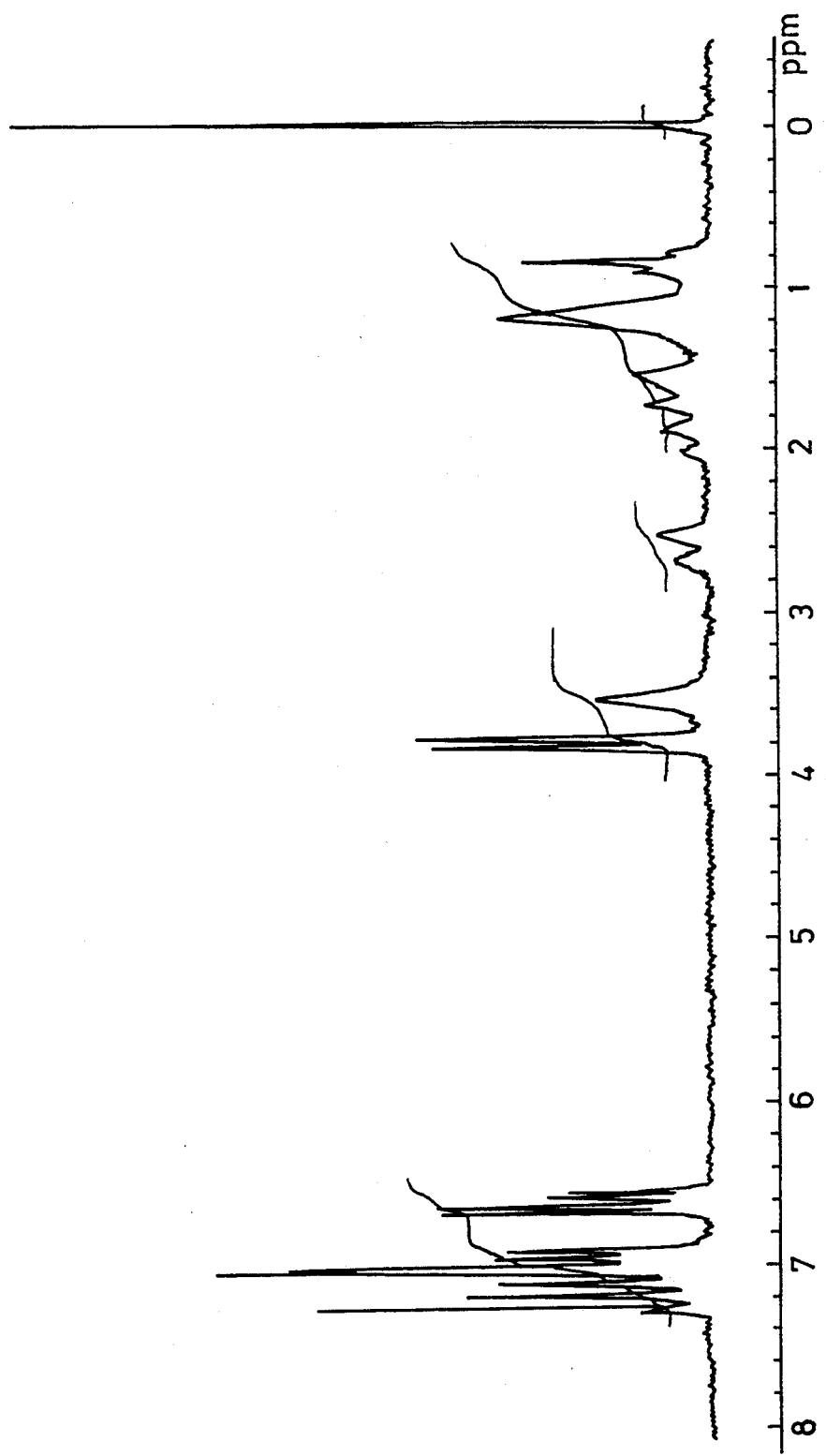

FIG. 6 is a $^1$H-NMR spectrum chart of the diamino compound obtained in Example 2.

Figure 7:
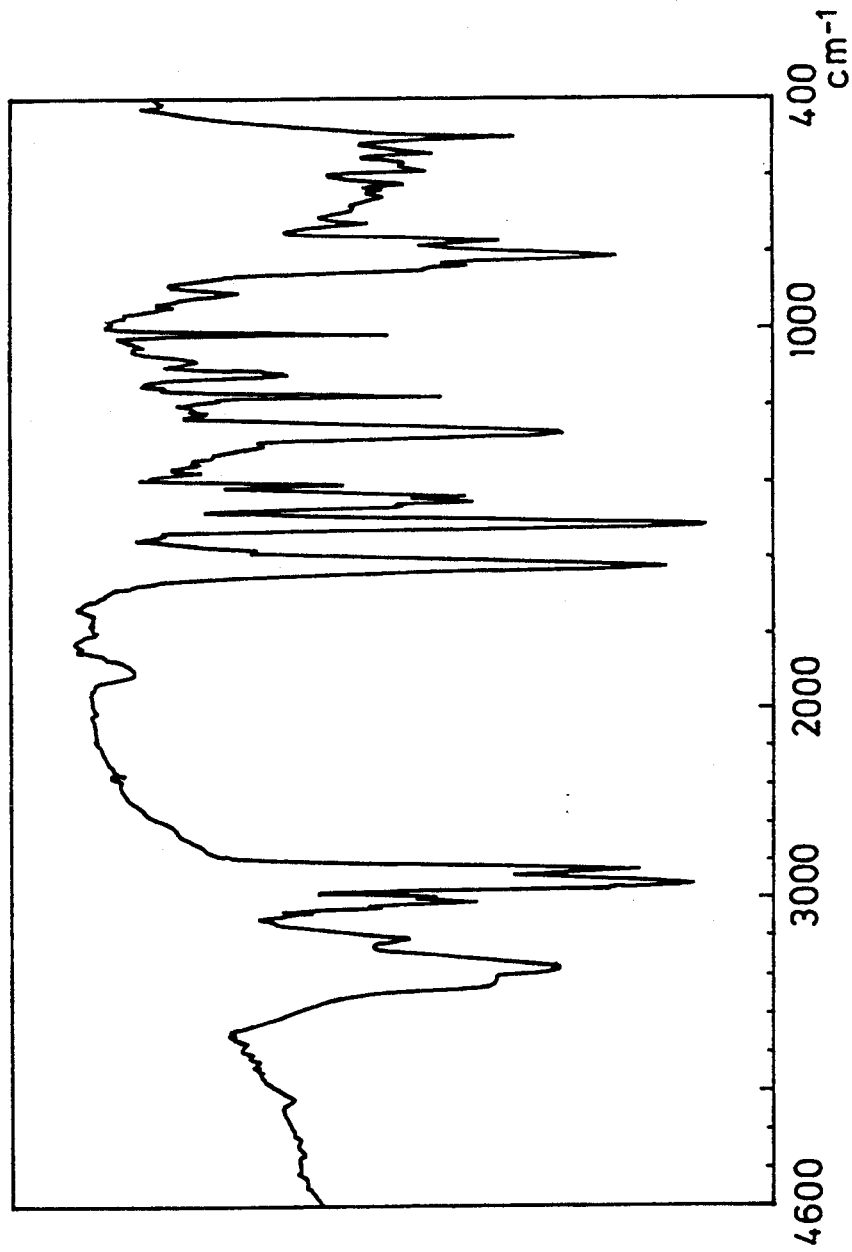

FIG. 7 is an IR chart of the diamino compound obtained in Example 2.

DESCRIPTION OF PREFERRED EMBODIMENTS

The following examples illustrate the compounds of the present invention more specifically by production examples. Further, the products obtained by using the compounds, namely liquid crystal alignment layers of polyimide resins, are described as examples, but these will not always be precise in practical applications.

Figure 1:
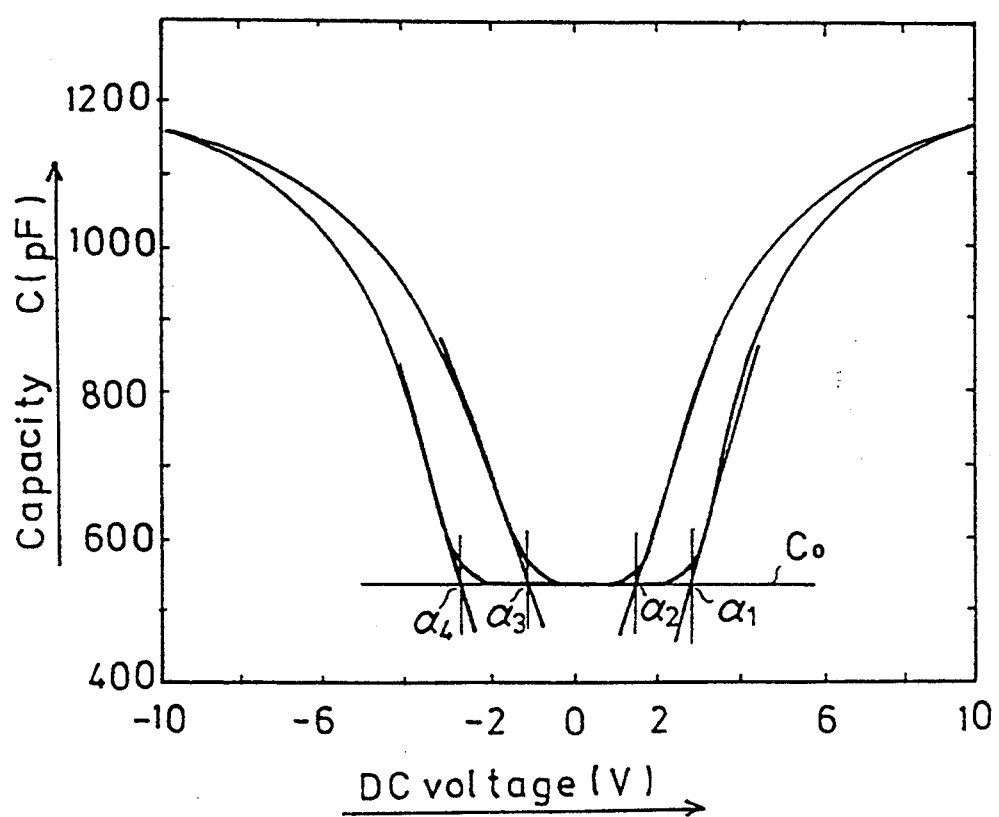
FIG. 1 is a graph showing C-V hysteresis curves.

In the following examples and comparative examples, the image-sticking phenomenon degrees were determined by using a C-V curve method. The C-V curve method was conducted by applying an alternating current of 25 mV and 1 kHz to a crystal cell and applying a direct current triangle wave (abbreviated as DC voltage hereinafter) of a frequency of 0.0036 Hz, sweeping the DC voltage within the limits of −10 V to 10 V and recording the change of capacity C. When the voltage is swept to a positive side (0→10 V), the capacity becomes high. Then, the voltage is swept to a negative side (10→0 V), and the capacity becomes low. In the same manner, when the voltage is swept to a side more negative than 0 (0→−10 V), the capacity becomes high. The voltage is swept to a positive side (−10→0 V), and the capacity becomes low. After repeating several cycles, the wave forms obtained are as shown in FIG. 1. When the electric charge differences formed on the alignment layer surface are stabilized, the voltage curves are hysteresis curves at the positive side and the negative side. A residual electric charge is determined by drawing tangent lines each C-V curve at the positive and negative sides, drawing a line of capacity ($C_0$) at 0 of the DC voltage, seeking each intersecting point ($α_1$–$α_4$) of the tangent lines and the line of capacity ($C_0$), calculating the voltage differences of each two points at the positive side $|α_1-α_2|$ and at the negative side $|α_3-α_4|$, and then calculating the average voltage difference, namely $(|α_1-α_2|+|α_3-α_4|)/2$. When the film thickness of the liquid crystal cell and the film thickness of the alignment layer are the same, the residual electric charge can be used as a parameter of the electric charge displacement and the stability. Namely, when alignment layers having smaller remaining electric charge are used, the image-sticking phenomenon of the liquid crystal display device can be reduced.

Figure 3:
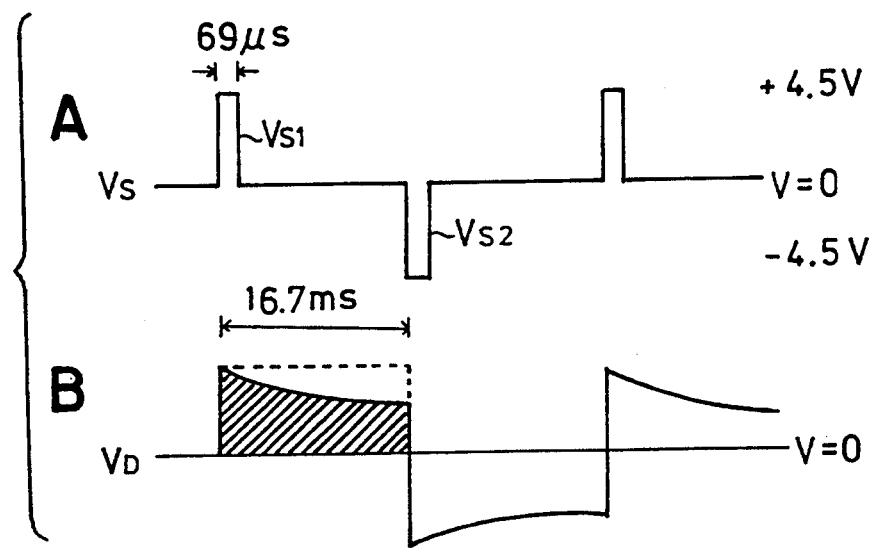
In FIG. 3, $V_S$ shows a rectangle wave having 69 μs of a gate pulse wide, 60 Hz of a frequency and ±4.5 V of a peak value.

The voltage holding ratios are measured by a circuit as shown in FIG. 2. In the measurement, a rectangle wave ($V_s$) having 69 μs of a gate pulse wide, 60 Hz of a frequency and ±4.5 V of a peak value is applied to a source to read change of a drain ($V_D$) by an oscilloscope. For example, when the rectangle wave is applied to the source, the drain ($V_D$) shows a positive value until the next negative rectangle wave is applied. If the holding rate is 100%, $V_D$ in FIG. 3 shows a rectangle orbit represented by a dotted line, while $V_D$ normally shows an orbit represented by a solid line which gradually approaches to zero. Then, an area of the measured orbit (an area surrounded by V=0 and the orbit), namely an oblique line part is calculated four times, and the average value is obtained. When the voltage is not decreased at all, supposing that the area is 100%, the relative value of the measured area is a voltage holding ratio.

Pretilt angles are determined by a crystal rotation method.

Production Example 1

Aluminum chloride 375.70 g and nitrobenzene 650 ml were mixed, the mixture was poured and dissolved in para-nitrobenzoyl chloride 212.00 g on ice cooling. Then, a solution of 1,1-diphenylcyclohexane 78.43 g in nitrobenzene 150 ml was added dropwise for 30 minutes. 30 minutes after adding, the ice bath was removed and the mixture was slowly heated to 75° C. for four hours in a mantle heater. The finish of the reaction was confirmed by liquid chromatography, and then the reaction solution was poured into ice 2.5 liters to extract with chloroform 1.0 liter. The solution was washed with a 6N-HCl solution, an aqueous solution of sodium bicarbonate, an aqueous solution of sodium chloride and water. After chloroform was removed with a rotary evaporator, nitrobenzene was removed by steam distillation. The residue was recrystallized with ethyl acetate to obtain 118.64 g of black purple crystals of 1,1-bis[4-(4-nitrobenzoyl)phenyl]cyclohexane. The melting point was 174.2°-176.1° C.

1,1-Bis[4-(4-nitrobenzoyl)phenyl]cyclohexane 106.63 g was dissolved in dichloromethane 1300 ml, and a solution of titanium tetrachloride 120 g in dichloromethane 200 ml was added dropwise for one hour. Then, a solution of triethylsilane 115.5 g in dichloromethane 150 ml was added dropwise for 90 minutes. When 30 minutes passed after the addition was finished, the ice bath was removed and the solution was stirred for four hours at room temperature. The finish of the reaction was confirmed by liquid chromatography, and then the reaction solution was neutralized with an aqueous solution of sodium carbonate and washed with water. After dichloromethane was removed with a rotary evaporator, the residue was dissolved in toluene, the solution was treated with an alumina column, and the solvent was distilled away from the elute. The concentrate was recrystallized with ethyl acetate solvent to obtain 93.5 g of pale yellow crystals of 1,1-bis[4-(4- nitrobenzyl)phenyl]cyclohexane. The melting point was 125.4°–126.5° C.

1,1-bis[4-(4-nitrobenzyl)phenyl]cyclohexane 98.93 g was dissolved in 1100 ml of tetrahydrofuran, a Pd—C catalyst (5% purity, water content 55.9%) 9.8 g was added, and the mixture was cooled with water at atmospheric pressure and contacted with hydrogen gas with stirring. After the absorption of hydrogen stopped, the catalyst was filtered off and the solution was concentrated. The concentrate was recrystallized with toluene solvent to obtain 71.71 g of 1,1-bis[4-(4aminobenzyl)-phenyl]cyclohexane which is a diamino compound of the present invention. The melting point was 154.4°–155.5° C.

The proton nuclear magnetic resonance spectrum ($^1$H-NMR) of this compound is shown in FIG. 4 and the IR chart is shown in FIG. 5.

Production Example 2

4,4-Diphenylcyclohexanone 54.0 g was dissolved with stirring in tetrahydrofuran 700 ml, which was purified dehydration, under nitrogen sealing and cooled with dry ice-acetone. Then, a solution 200 ml of n-butyl lithium (1.6 mole/liter) in hexane was added dropwise for two hours. Two hours after adding, the ice bath was removed and the mixture was slowly heated to room temperature for four hours. The finish of the reaction was confirmed by liquid chromatography, then a saturated ammonium chloride aqueous solution 300 ml was poured into the reaction solution and the mixture was extracted with toluene 700 ml. The solution was washed with an aqueous solution of sodium chloride and toluene was removed with a rotary evaporator. Then, the residue was dissolved in toluene 400 ml, an ion exchange resin (Amberlist 15E, manufactured by ORGANO Co, Ltd.) 2.8 g was mixed, and the mixture was heated under reflux for three hours. The ion exchange resin was filtered off, toluene was removed with a rotary evaporator, the residue was dissolved in toluene/heptane ¼ (v/v) and the solution was purified with a silica gel column to obtain 4,4-diphenyl-1-butylcyclohexene (containing 4,4-diphenyl-1-butylidenecyclohexane) 32.97 g.

4,4-diphenyl-1-butylcyclohexene (containing 4,4-diphenyl-1-butylidenecyclohexane) 32.0 g was dissolved in tetrahydrofuran 200 ml and acetic acid 300 ml, platinum oxide 1.0 g was added, and the mixture was cooled with water at atmospheric pressure and contacted to hydrogen gas with stirring. After the absorption of hydrogen was stopped, the catalyst was filtered off, water two liters was added to the solution, and the solution was extracted with toluene one liter. The extracted solution was washed with water, toluene was removed with a rotary evaporator and 1,1-diphenyl-4-butylcyclohexane 30.58 g was obtained.

Aluminum chloride 101.22 g and nitrobenzene 200 ml were mixed, the mixture was poured and dissolved in para-nitrobenzoyl chloride 57.10 g on ice cooling. Then, a solution of 1,1-diphenyl-4-butylcyclohexane 30.0 g in nitrobenzene 50 ml was added dropwise for 30 minutes. 30 minutes after adding, the ice bath was removed and the mixture was slowly heated to 67° C. for four hours in a mantle heater. The finish of the reaction was confirmed by liquid chromatography, and then the reaction solution was poured into ice 1.5 liters to extract with chloroform 1.0 liter. The solution was washed with a 6N-HCl solution, an aqueous solution of sodium bicarbonate, an aqueous solution of sodium chloride and water. After chloroform was removed with a rotary evaporator, nitrobenzene was removed by steam distillation. The residue was dissolved in toluene, and the solution was purified with a silica gel column to obtain 1,1-bis[4-(4-nitrobenzoyl)phenyl]-4-butylcyclohexane 45.40 g.

1,1-Bis[4-(4-nitrobenzoyl)phenyl]-4-butylcyclohexane 45.40 g was dissolved in dichloromethane 660 ml, and a solution of trifluorosulfuric acid 36.9 g in dichloromethane 860 ml was added dropwise for one hour. Then, a solution of triethylsilane 47.38 g in dichloromethane 80 ml was added dropwise for 90 minutes. When 30 minutes passed after the addition was finished, the ice bath was removed and the solution was stirred for five hours at room temperature. The finish of the reaction was confirmed by liquid chromatography, and then the reaction solution was neutralized with an aqueous solution of sodium carbonate and washed with water. After dichloromethane was removed with a rotary evaporator, the residue was dissolved in toluene, the solution was treated with an alumina column, and the solvent was distilled away from the elute to obtain 1,1-bis[4-(4-nitrobenzyl)phenyl]-4-butylcyclohexane 38.0 g.

1,1-Bis[4-(4-nitrobenzyl)phenyl]-4-butylcyclohexane 38.0 g was dissolved in 500 ml of tetrahydrofuran, a Pd—C catalyst (5% purity, water content 55.9%) 4.0 g was added, and the mixture was cooled with water at atmospheric pressure and contacted with hydrogen gas with stirring. After the absorption of hydrogen stopped, the catalyst was filtered off and the solution was concentrated. The concentrate was recrystallized with mixture solvent of ethanol 87% and methanol 13% to obtain 1,1-bis[4-(4-aminobenzyl)phenyl]-4-butylcyclohexane 14.22 g which is a diamino compound of the present invention. The melting point was 58.5°–60.1° C.

The proton nuclear magnetic resonance spectrum ($^1$H-NMR) of this compound is shown in FIG. 6 and the IR chart is shown in FIG. 7.

EXAMPLE 1

To a four-necked flask equipped with a stirrer, a thermometer, a condenser and a nitrogen displace apparatus, N-methyl-2-pyrrolidone 50 g which was purified by dehydration, and then 1,1-bis[4-(4-aminobenzyl)-phenyl]cyclohexane 7.43 g were charged and dissolved with stirring. The mixture was cooled to 13° C., pyromellitic dianhydride 3.69 g was added, and the mixture was reacted with stirring on cooling. After one hour, para-aminophenyltrimethoxysilane 0.11 g was added, and the mixture was reacted with stirring for one hour at 20° C.

Then, the reaction solution was diluted with N-methyl-2-pyrrolidone (NMP) 51.1 g to obtain a transparent solution of 10% by weight of polyamic acid. The viscosity of the solution was 1870 centipoises at 25° C.

A mixture solution of 1:1 of butyl Cellosolve and NMP was added to the solution to dilute the solution of polyamic acid to 3% by weight, and the solution was applied by a rotation coating method (a Spinner method) on transparent glass substrates equipped with ITO electrodes at the one sides. The coating conditions were 5000 rpm and 15 seconds. After coating, the substrates were dried at 100° C. for ten minutes, heated to 200° C. for one hour in an oven, and treated at 200° C. for 90 minutes to obtain polybenzylimide having film thickness of about 600 angstroms. The film surface of two pieces of the substrates on which the polybenzylimide films were formed was rubbed, respectively, to obtain liquid crystal alignment layers. A liquid crystal cell having thickness of 6 microns was assembled by the substrates so as to be oriented in parallel and anti parallel rubbing directions. Liquid crystal FB01 for TFT manufactured by CHISSO CORPORATION was injected into the liquid crystal cell. Then, the liquid crystal was isotropic-treated with heating at 120° C. for 30 minutes and cooled to room temperature to obtain a liquid crystal device. To determine the pretilt angle, a liquid crystal cell having thickness of 20 microns in which liquid crystal ZLI-1132 manufactured by Merck Company was injected was similarly prepared.

The aligning properties of the liquid crystal device were good, and the pretilt angle of the liquid crystal was 7.3 degrees by the crystal rotation method. The residual electric charge determined was 0.06 V at 25° C. and the voltage holding ratio was 97.4%.

EXAMPLE 2

To a 200 ml four-necked flask equipped with a stirrer, a thermometer, a condenser and a nitrogen displace apparatus, N-methyl-2-pyrrolidone 50 g, which was purified by dehydration, and 1,1-bis[4-(4aminobenzyl)-phenyl]cyclohexane 7.43 g were charged, and the mixture was dissolved with stirring. The mixture was cooled to 13° C., methylcyclobutane tetracarboxylic acid dianhydride 3.68 g was charged at one time, and the mixture was reacted with stirring on cooling. After one hour, para-aminophenyltrimethoxysilane 0.33 g was added, and the mixture was reacted with stirring for one hour at 20° C.

Then, the reaction solution was diluted with N-methyl-2-pyrrolidone (NMP) 53.0 g to obtain a transparent solution of 10% by weight of polyamic acid. The viscosity of the solution was 104.5 centipoises at 25° C.

A mixture solution of 7:3 of butyl Cellosolve and NMP was added to the solution to dilute the solution of polyamic acid to 3% by weight, and the solution was applied by a rotation coating method (a Spinner method) on transparent glass substrates equipped with ITO electrodes at the one sides. The coating conditions were 3000 rpm and 15 seconds. After coating, the substrates were dried at 100° C. for ten minutes, heated to 200° C. for one hour in an oven, and treated at 200° C. for 90 minutes to obtain polybenzylimide having film thickness of about 600 angstroms. The film surface of two pieces of the substrates on which the polybenzylimide films were formed was rubbed, respectively, to obtain liquid crystal alignment layers. A liquid crystal cell having thickness of 6 microns was assembled by the substrates so as to be oriented in parallel and anti parallel rubbing directions. Liquid crystal FB01 for TFT manufactured by CHISSO CORPORATION was injected into the liquid crystal cell. Then, the liquid crystal was isotropic-treated with heating at 120° C. for 30 minutes and cooled to room temperature to obtain a liquid crystal device. To determine the pretilt angle, a liquid crystal cell having thickness of 20 microns in which liquid crystal ZLI-1132 manufactured by Merck Company was injected was similarly prepared.

The aligning properties of the liquid crystal device were good, and the pretilt angle of the liquid crystal was 3.1 degrees by the crystal rotation method. The residual electric charge determined was 0.01 V at 25° C. and the voltage holding ratio was 97.3%.

EXAMPLE 3

To a 200 ml four-necked flask equipped with a stirrer, a thermometer, a condenser and a nitrogen displace apparatus, N-methyl-2-pyrrolidone 50 g, which was purified by dehydration, and 1,1-bis[4-(4-aminobenzyl)-phenyl]-4-butylcyclohexane 8.36 g were charged, and the mixture was dissolved with stirring. The mixture was cooled to 13° C., pyromellitic acid dianhydride 3.69 g was charged at one time, and the mixture was reacted with stirring on cooling. After one hour, para-aminophenyltrimethoxysilane 0.11 g was added, and the mixture was reacted with stirring for one hour at 20° C.

Then, the reaction solution was diluted with N-methyl-2-pyrrolidone (NMP) 59.4 g to obtain a transparent solution of 10% by weight of polyamic acid. The viscosity of the solution was 1540 centipoises at 25° C.

A mixture solution of 1:1 of butyl Cellosolve and NMP was added to the solution to dilute the solution of polyamic acid to 3% by weight, and the solution was applied by a rotation coating method (a Spinner method) on transparent glass substrates equipped with ITO electrodes at the one sides. The coating conditions were 5000 rpm and 15 seconds. After coating, the substrates were dried at 100° C. for ten minutes, heated to 200° C. for one hour in an oven, and treated at 200° C. for 90 minutes to obtain polybenzylimide having film thickness of about 600 angstroms. The film surface of two pieces of the substrates on which the polybenzylimide films were formed was rubbed, respectively, to obtain liquid crystal alignment layers. A liquid crystal cell having thickness of 6 microns was assembled by the substrates so as to be oriented in parallel and anti parallel rubbing directions. Liquid crystal FB01 for TFT manufactured by CHISSO CORPORATION was injected into the liquid crystal cell. Then, the liquid crystal was isotropic-treated with heating at 120° C. for 30 minutes and cooled to room temperature to obtain a liquid crystal device. To determine the pretilt angle, a liquid crystal cell having thickness of 20 microns in which liquid crystal ZLI-1132 manufactured by Merck Company was injected was similarly prepared.

The aligning properties of the liquid crystal device were good, and the pretilt angle of the liquid crystal was 5.0 degrees by the crystal rotation method. The residual electric charge determined was 0.07 V at 25° C. and the voltage holding ratio was 95.6%.

Comparative Example 1

A polyamic acid solution was obtained by polymerization of 2,2-bis[4-(4-aminophenoxy)phenyl]propane 8.06 g, pyromellitic dianhydride 4.36 g and para-aminophenyltrimethoxysilane 0.11 g.

After a mixture solution of 1:1 of butyl Cellosolve and NMP was added to the solution to dilute the polyamic acid to 3% by weight, the solution was applied by a rotation coating method (a Spinner method) on transparent glass substrates equipped with ITO electrodes at the one sides. The coating conditions were 3000 rpm and 15 seconds. After coating the substrates were dried at 100° C. for ten minutes, heated to 200° C. for one hour in an oven, and treated at 200° C. for 90 minutes to obtain polyetherimide having film thickness of about 600 angstroms. The film surface of two pieces of the substrates on which the polyetherimide films were formed was rubbed, respectively, to obtain liquid crystal alignment layers. A liquid crystal cell having thickness of 6 microns was assembled by the substrates so as to be oriented in parallel and anti parallel rubbing directions. Liquid crystal FB01 for TFT manufactured by CHISSO CORPORATION was injected into the liquid crystal cell. Then, the liquid crystal was isotropic-treated with heating at 120° C. for 30 minutes and cooled to room temperature to obtain a liquid crystal device. To determine the pretilt angle, a liquid crystal cell having thickness of 20 microns in which liquid crystal ZLI-1132 manufactured by Merck Company was injected was similarly prepared.

The aligning properties of the liquid crystal device were good, and the pretilt angle of the liquid crystal was 3.7 degrees by the crystal rotation method. The residual electric charge determined was 0.20 V at 25° C. and the voltage holding ratio was 90.0%.

Comparative Example 2

A polyamic acid solution was obtained by polymerization of 2,2-bis[4-(4-aminophenoxy)phenyl]propane 8.06 g, methylcyclobutanetetracarboxylic acid dianhydride 3.92 g and para-aminophenyltrimethoxysilane 0.11 g.

After a mixture solution of 7:3 of butyl Cellosolve and NMP was added to the solution to dilute the polyamic acid to 3% by weight, the solution was applied by a rotation coating method (a Spinner method) on transparent glass substrates equipped with ITO electrodes at the one sides. The coating conditions were 5000 rpm and 15 seconds. After coating the substrates were dried at 100° C. for ten minutes, heated to 200° C. for one hour in an oven, and treated at 200° C. for 90 minutes to obtain polyetherimide having film thickness of about 600 angstroms. The film surface of two pieces of the substrates on which the polyetherimide films were formed was rubbed, respectively, to obtain liquid crystal alignment layers. A liquid crystal cell having thickness of 6 microns was assembled by the substrates so as to be oriented in parallel and anti parallel rubbing directions. Liquid crystal FB01 for TFT manufactured by CHISSO CORPORATION was injected into the liquid crystal cell. Then, the liquid crystal was isotropic-treated with heating at 120° C. for 30 minutes and cooled to room temperature to obtain a liquid crystal device. To determine the pretilt angle, a liquid crystal cell having thickness of 20 microns in which liquid crystal ZLI-1132 manufactured by Merck Company was injected was similarly prepared.

The aligning properties of the liquid crystal device were good, and the pretilt angle of the liquid crystal was 1.5 degrees by the crystal rotation method. The residual electric charge determined was 0.15 V at 25° C. and the voltage holding ratio was 89.0%.

Comparative Example 3

A polyamic acid solution was obtained by polymerization of 4,4-diaminophenylether 3.46 g, pyromellitic dianhydride 4.36 g and para-aminophenyltrimethoxysilane 0.11 g.

After a mixture solution of 1:1 of butyl Cellosolve and NMP was added to the solution to dilute the polyamic acid to 3% by weight, the solution was applied by a rotation coating method (a Spinner method) on transparent glass substrates equipped with ITO electrodes at the one sides. The coating conditions were 3000 rpm and 15 seconds. After coating the substrates were dried at 100° C. for ten minutes, heated to 200° C. for one hour in an oven, and treated at 200° C. for 90 minutes to obtain polyetherimide having film thickness of about 600 angstroms. The film surface of two pieces of the substrates on which the polyetherimide films were formed was rubbed, respectively, to obtain liquid crystal alignment layers. A liquid crystal cell having thickness of 6 microns was assembled by the substrates so as to be oriented in parallel and anti parallel rubbing directions. Liquid crystal FB01 for TFT manufactured by CHISSO CORPORATION was injected into the liquid crystal cell. Then, the liquid crystal was isotropic-treated with heating at 120° C. for 30 minutes and cooled to room temperature to obtain a liquid crystal device. To determine the pretilt angle, a liquid crystal cell having thickness of 20 microns in which liquid crystal ZLI-1132 manufactured by Merck Company was injected was similarly prepared.

The aligning properties of the liquid crystal device were good, and the pretilt angle of the liquid crystal was 0.5 degrees by the crystal rotation method. The residual electric charge determined was 0.90 V at 25° C. and the voltage holding ratio was 78.0%.

According to the present invention, new diamino compounds and method for producing these compounds are provided.

It is found that the polyimide compounds obtained by using the diamino compounds as raw materials have excellent properties as liquid crystal alignment layers, and that the polyimide compounds can be changed into liquid crystal alignment layers having uniform and high pretilt angles over the whole display surface of the wide substrates, which are required to STN liquid crystal display devices by conventional rubbing treatment. Further, the liquid crystal display devices using the liquid crystal alignment layers have excellent quality with a high voltage holding ratio and without an image-sticking phenomenon. It is considered that these effects are brought by a phenylcyclohexane ring and an alkyl group bonded to the ring of the diamino compounds of the raw materials. The diamino compounds of the present invention having the above characteristics are designed as raw materials of liquid crystal alignment layers. Further, these compounds can be used for the other polymer compounds such as polyimides and polyamides and their property modification. It is expected to use for the other epoxy crosslinking materials or to introduce new characteristic properties into polymer compounds.

We claim:

1. A diamino compound represented by a general formula (1):

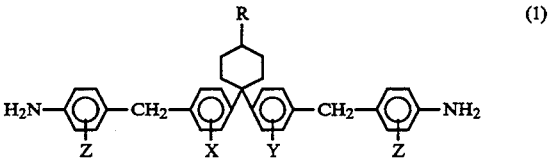

wherein R indicates hydrogen or an alkyl group having 1 to 8 carbon atoms, further, X, Y and Z indicate hydrogen, an alkyl group having 1 to 3 carbon atoms or fluorine, respectively, and a part or all of them may be the same or different, and the positions of these substitutive groups may be ortho positions or meta positions.

2. A method for producing a diamino compound represented by the general formula (1) in claim 1, which comprises condensing a para nitrobenzoyl chloride derivative represented by the formula (3):

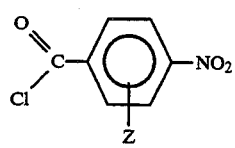

wherein Z indicates hydrogen, an alkyl group having 1 to 3 carbon atoms or fluorine, and the position of substitutive group Z may be an ortho position or a meta position, to a diphenylcyclohexane derivative represented by the formula (2):

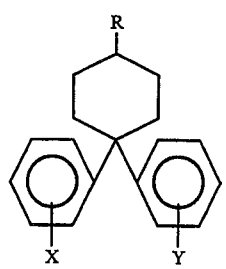

wherein R indicates hydrogen or an alkyl group having 1 to 8 carbon atoms, further, X and Y indicate hydrogen, an alkyl group having 1 to 3 carbon atoms or fluorine, respectively, and a part or all of them may be the same or different, and the positions of these substitutive groups may be ortho positions or meta positions, and reducing a carbonyl group and a nitro group to obtain the diamino compound.

* * * * *